United States Patent
Anquez et al.

(10) Patent No.: US 12,296,203 B2
(45) Date of Patent: May 13, 2025

(54) METHOD FOR TREATING A PATIENT WITH HIFU

(71) Applicant: THERACLION SA, Malakoff (FR)

(72) Inventors: Jérémie Anquez, Paris (FR); Anthony Grisey, Saint Cyr l'Ecole (FR); Björn Gerold, Versailles (FR)

(73) Assignee: THERACLION SA, Malakoff (FR)

( * ) Notice: Subject to any disclaimer, the term of this patent is extended or adjusted under 35 U.S.C. 154(b) by 709 days.

(21) Appl. No.: 17/619,692

(22) PCT Filed: Jun. 17, 2020

(86) PCT No.: PCT/EP2020/066780
§ 371 (c)(1),
(2) Date: Dec. 16, 2021

(87) PCT Pub. No.: WO2020/254419
PCT Pub. Date: Dec. 24, 2020

(65) Prior Publication Data
US 2022/0305298 A1    Sep. 29, 2022

(30) Foreign Application Priority Data

Jun. 19, 2019   (EP) .................................... 19315043

(51) Int. Cl.
*A61N 7/02*   (2006.01)
*A61B 18/00*   (2006.01)

(52) U.S. Cl.
CPC ...... *A61N 7/02* (2013.01); *A61B 2018/00345* (2013.01); *A61B 2018/00577* (2013.01); *A61B 2018/00589* (2013.01)

(58) Field of Classification Search
CPC .......... A61B 2017/00154; A61B 2018/00023; A61B 2018/00345; A61B 2018/00577; A61B 2018/00589; A61B 2090/378; A61N 2007/0039; A61N 7/02
See application file for complete search history.

(56) References Cited

U.S. PATENT DOCUMENTS

| 7,588,547 | B2 * | 9/2009 | Deem ................. A61N 1/0492 424/9.5 |
| 2002/0032394 | A1 * | 3/2002 | Brisken .............. A61B 17/2202 601/2 |
| 2004/0153126 | A1 | 8/2004 | Okai |

(Continued)

FOREIGN PATENT DOCUMENTS

WO    2020254419    12/2020

OTHER PUBLICATIONS

Serrone Joseph et al., "The Potential Applications of High-Intensity Focused Ultrasound (HIFU) in Vascular Neurosurgery", Journal of Clinical Neuroscience, Jul. 2011, vol. 19, 8 pages.

(Continued)

*Primary Examiner* — Michael F Peffley
(74) *Attorney, Agent, or Firm* — Finch & Maloney PLLC

(57) ABSTRACT

A method of performing a heat treatment of blood vessels (6), such as varicose veins, in order to coagulate the vessel walls (2). Bubbles (4) are selectively created in the blood (3), such that the formation of blood coagula is avoided during the treatment due to cavitation (5).

15 Claims, 3 Drawing Sheets

(56) References Cited

U.S. PATENT DOCUMENTS

Figure 1:
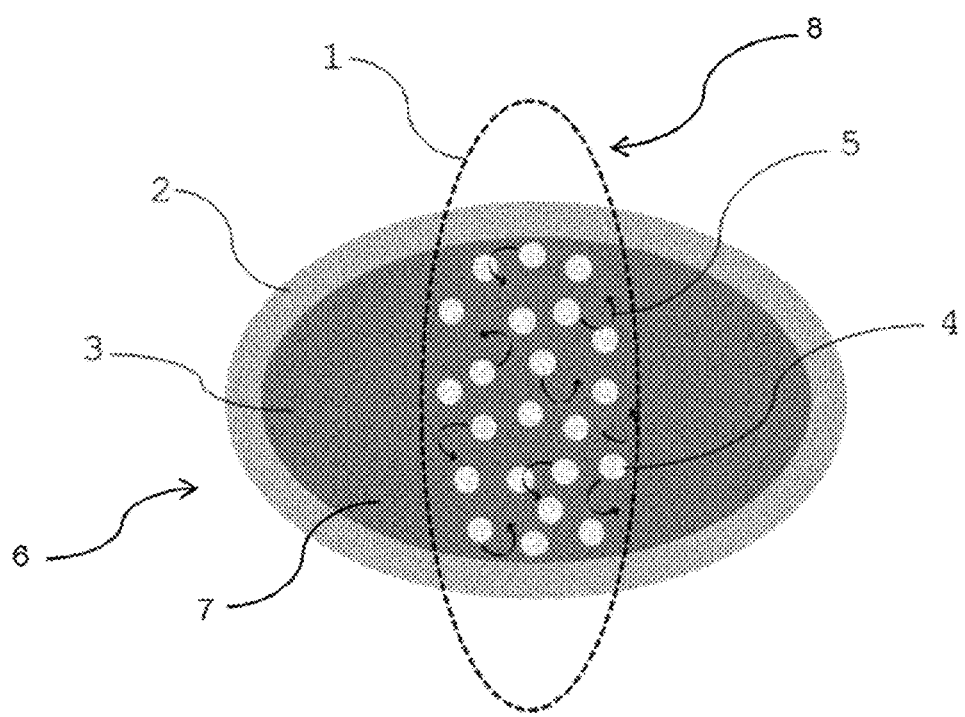

| | | | | |
|---|---|---|---|---|
| 2007/0088346 A1* | 4/2007 | Mirizzi | .................... | A61N 7/02 |
| | | | | 606/27 |
| 2007/0161902 A1* | 7/2007 | Dan | ................. | A61B 17/2200 |
| | | | | 4 |
| | | | | 600/458 |
| 2016/0339273 A1* | 11/2016 | Al Mayiah | .............. | A61N 7/02 |

OTHER PUBLICATIONS

International Search Report and the Written Opinion of the International Searching Authority for International Application No. PCT/EP2020/066780 mailed Sep. 9, 2020, 19 pages.

* cited by examiner

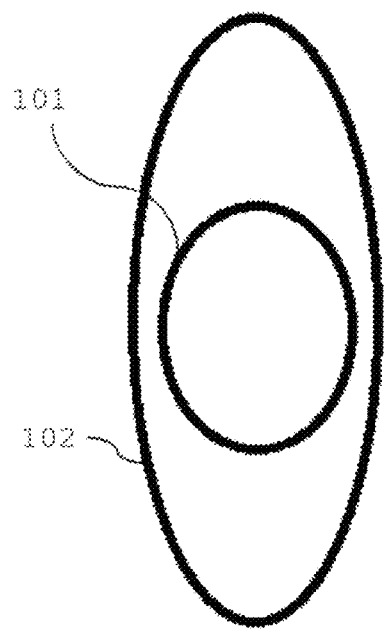
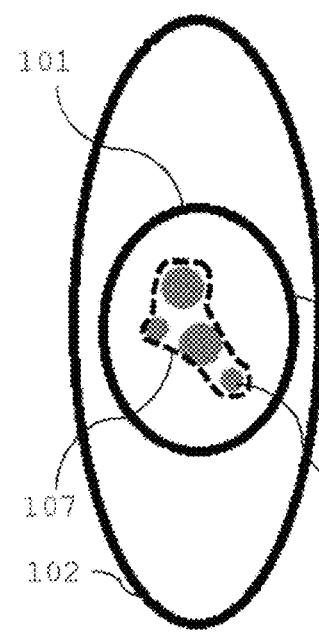
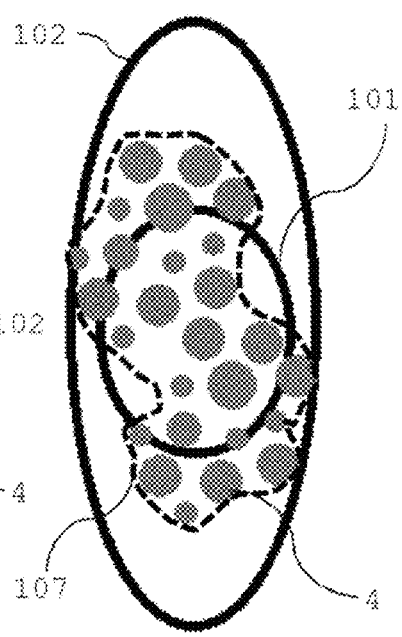
Fig. 4a Fig. 4b Fig. 4c
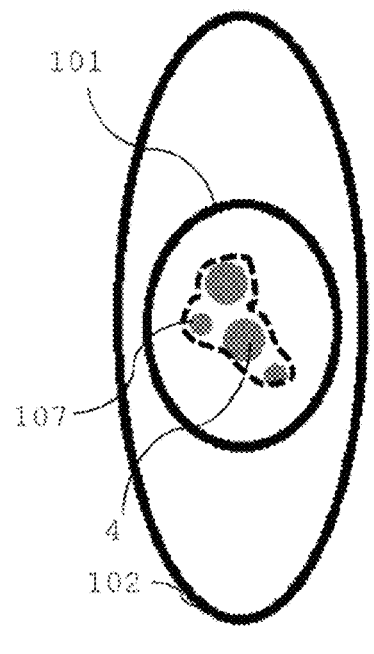
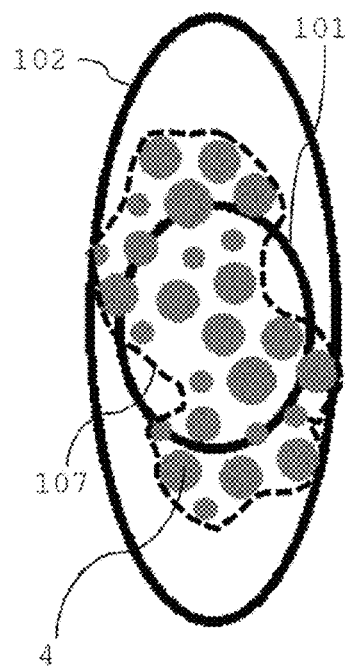
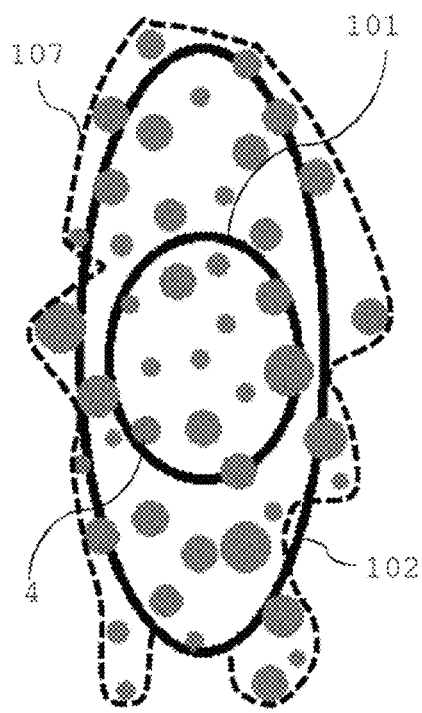
Fig. 5a Fig. 5b Fig. 5c

METHOD FOR TREATING A PATIENT WITH HIFU

The invention relates to a method for treating a patient by thermal ablation of blood vessels by HIFU according to the preamble of the independent patent claim.

It is known to use heat treatments for the occlusion of veins, e.g. for the treatment of varicose veins.

U.S. Pat. No. 8,214,052 discloses an invasive method for treating a vein with a catheter which therefore delivers heat to the vein wall. The catheter is positioned within the vein segment to be treated, is heated and withdrawn from the vein.

The main drawback of this method is that the catheter has to be invasively inserted in the vein segment to be treated, which carries a risk of perforation and is a complex process for tortuous veins.

HIFU devices, at the contrary, allow the non-invasive treatment of targets within a patient's body.

Mechanical or thermal effects are potential mechanisms for HIFU treatments of veins. Mechanical effects rely on damaging the endothelium of the vessel to promote thrombus formation and induce occlusion. This method has not been proven to be efficient without adjuvants (Hwang et al. 2005, 2006, 2010; Zhou et al. 2011).

Thermal effects can also damage the endothelium but are more efficient since the damages may extend to the other layers of the vein wall (media, adventitia) and thermal denaturation of the collagen results in a beneficial lumen shrinkage. Other thermal methods (laser, radiofrequency) are now widely accepted.

HIFU thermal ablation is most effective when the blood flow is reduced to a minimum to avoid the heat sink effect. A combination of cavitation and heating effects was described in the literature (Hynynen et al. 1996), where mechanical effects were used to induce a vasospasm, thus stopping the blood flow and putting the vessel in a favorable configuration for subsequent thermal pulses. Complete collapse of the vein is sometimes considered preferable since the heat deposition may induce blood coagulation (i.e. formation of so-called «thermal coagulum», at temperatures above 70° C., as described in Heger 2014. However, complete collapse of the vein is difficult to reliably achieve. Hence there is a risk that the thermal coagulum is flushed, inducing pulmonary embolism or other systemic side effects.

It is the object of the present invention to overcome the disadvantages of the prior art, in particular to provide a method of treating a vein that reduces the risk of embolism and other side effects during or after the HIFU treatment.

This and other objects are solved by a method according to the characterizing portion of the independent claim.

According to the invention, a method for treating a patient by thermal ablation of blood vessels by HIFU is provided. The treatment is carried out by a sonication with at least one HIFU pulse. At least one characteristic (for example, the intensity, duration, and/or waveform) of at least one of said pulses is chosen such as to create bubbles within the blood inside the vessel and such as to thermally coagulate at least a part of the wall of the targeted vessel, preferably without inducing rupture of the vein wall.

The method allows thermally occluding a partially collapsed vessel by using HIFU so that bubble activity (cavitation and/or boiling) caused by the HIFU is present during the pulse. This prevents mechanically the formation of a significant blood clot. The underlying mechanism is that micro-streaming produced by the bubbles does not allow for an agglomeration of blood contents to form a significant thermal coagulum of the blood.

In a preferred embodiment, the characteristics of at least one pulse are adapted such as to create bubbles at blood temperatures that do not cause thermal coagulation in the blood, preferably at temperatures below 70° C.

Additionally or alternatively, the intensity of at least one pulse is such that the blood is heated, at least temporarily, to a blood temperature that is high, in particular a blood temperature that would cause thermal coagulation in the absence of bubbles, preferably a temperature above 70° C. Preferably, the intensity is such that bubble activity is constantly present.

Constant bubble activity shall be understood as an activity without interruption until the end of a pulse once the activity has started. In particular, it shall encompass cases where cavitation does not start instantaneously but, once it has begun, it does not stop until the end of the pulse. Alternatively, cases where cavitation occurs at the very beginning of the pulse (after a few ultrasonic cycles have reached the focus) shall be encompassed as well.

In a preferred embodiment of the method, the mechanical index is kept above 1.9 during the whole thermal sonication. Preferably, the mechanical index is kept above 3 during the whole thermal sonication. The mechanical index MI is defined as $MI=PNP/(\text{square root } Fc)$, where PNP is the peak negative pressure of the ultrasound wave (MPa), derated by $0.3 \text{ dB} \cdot \text{cm}^{-1} \cdot \text{MHz}^{-1}$ to account for the difference between in-water and in-tissue acoustic attenuation, and Fc is the center frequency of the ultrasound wave (MHz).

Alternatively, the intensity is not constant, and cavitation can be triggered intermittently by high-intensity bursts.

In another preferred embodiment, the mechanical index is hence intermittently above 1.9 during the thermal sonication. Preferably, the mechanical index is intermittently above 3 during the thermal sonication.

In a preferred embodiment, bubbles are created by amplitude modulation (i.e. with a signal having an amplitude varying over time) intermittently or continuously. Alternatively or additionally, cavitation can be triggered by frequency modulation (i.e. with a signal having a frequency varying over time) intermittently or continuously.

In a preferred embodiment, the method additionally comprises a monitoring step performed by a monitoring means that is adapted to image the area that is being treated. A monitoring means is preferably selected from the group of B-mode, MRI, A-mode, color Doppler, duplexes (combination of color Doppler and B-mode), triplex (combination of color Doppler, B-mode and elastography), photoacoustics, other methods based on ultrasound, and optical methods using visible light. In particular, the monitoring means is adapted to assess the vein geometry and the vein position relative to the focal spot of the HIFU pulses (B-mode, MRI, A-mode, light).

Preferably, the intensity of the at least one pulse is chosen based on a manual control or automatic feedback loop from the monitoring means, such as reflected power or B-mode visual information, such as to create bubble activity (e.g. visible as a hyperechoic mark).

For example, a measurement of the reflected power may show that cavitation is insufficient at the selected treatment characteristics and the intensity of the HIFU is increased. In an alternative example, B-mode imaging may reveal the creation of more bubble activity than necessary, for example determined by the size of a hyperechoic mark, and the HIFU intensity would be reduced. Other monitoring means that allow for a detection of bubble activity may be employed, and other treatment characteristics (for example, pulse duration, frequency, shape of the beam, amplitude or frequency modulation parameters) than the HIFU power may be changed based on the monitoring means.

In a particularly preferred embodiment, at least two zones are defined. A first zone represents a minimum size of an area where a cavitation, boiling and/or bubble activity should occur. A second zone represents a maximum size of an area where the cavitation, boiling and/or bubble activity should occur.

The device may be adapted to overlay the first and second zones over an ultrasound image, in particular a B-mode image.

Thus, the device may be adapted to deliver a first HIFU dose at a treatment location. The first and second zones are defined such that the treatment location is positioned within, preferably substantially centered, in the first and second zones. The first zone is positioned entirely within the second zones. The first HIFU dose may preferably be delivered with treatment characteristics, in particular power, pulse duration, and/or pulse frequency, chosen such that no bubble activity, cavitation or boiling occurs. It will be understood that bubble activity, cavitation of boiling below a certain threshold caused by the first HIFU dose would not impair the treatment and is thus within the scope of the invention. The threshold below which such bubble activity, cavitation and/or boiling may be acceptable for the treatment may in particular be represented by the second zone.

Subsequently, a second HIFU dose is delivered wherein the treatment characteristics are changed to enhance bubble activity, cavitation or boiling. For example, the power, the pulse duration and/or the pulse frequency may be increased. The bubble activity, cavitation or boiling is detected as a hyperechoic mark (HEM). The device or the user may compare the size of a hyperechoic mark to the first zone and preferably to the second zone.

In particular, the device may use the surface area of the HEM, a position of the upper border of the HEM, a length of the HEM along one axis, in particular a treatment axis and/or an axis perpendicular the treatment axis, or any combination of these characteristics. Additionally or alternatively, derived characteristics such as a volume or an equivalent radius may be calculated.

The equivalent radius of a shape represents the radius of a circle with the same surface area as the shape.

If the size and/or location of the hyperechoic mark with respect to the first zone fulfil a first criterion, the treatment at the first location is terminated and the device moves the treatment to a second treatment location. Thus, the first criterion represents treatment conditions that provide a sufficiently effective treatment, in particular a treatment that creates sufficient bubbling activity, cavitation and/or boiling to prevent to formation of a thermal coagulum.

If the first criterion is not fulfilled, the last step is repeated, i.e. the treatment characteristics are adjusted and another pulse delivered. This procedure is repeated until the first criterion is fulfilled.

In one method according to the invention, the first criterion is that the hyperechoic mark is larger than the first zone based on its area. Alternatively, the first criterion may be that the hyperechoic mark extends beyond the first zone at at least one point, i.e. that at least some bubbles are located outside of the first zone. Additionally or alternatively, the first criterion may further include a condition that the hyperechoic mark extends beyond the first zone at at least one particular location, for example at a point closest to a treatment head, or at two points on substantially opposite sides of the circumference of the first zone.

At the second treatment location, the device may deliver a HIFU dose with treatment characteristics corresponding to the last delivered dose at the first location. The device may then compare the hyperechoic mark to the first and second zones of the second treatment location. The first and second zones of the second treatment location substantially correspond to the first and second zones of the first treatment location, but are defined such that the second treatment location is within, preferably centered in, the first and second zones.

After the delivery of the first HIFU dose at the second treatment location, the further treatment is defined depending on a second criterion. The second criterion is similar to the first criterion, but is defined with respect to the second zone and generally requires that bubbles be present only within the second zone. Thus, the second criterion may, preferably, be the logical negative of the first condition but with respect to the second zone.

The second criterion in particular represents an upper level of desirable treatment conditions.

Regardless of the condition that defines the first and second criterion, both the first and the second criterion are preferably independently checked at each treatment location and preferably after each HIFU dose.

Thus, the second criterion may be that the hyperechoic mark is smaller than the second zone based on its area. Alternatively, the second criterion may be that the hyperechoic mark does not extend beyond the second zone a particular point, i.e. that no bubbles are located outside of the second zone. Alternatively, the second criterion may include a condition that the hyperechoic mark does not extend beyond the second zone at at least one particular location, for example at a point closest to a treatment head, or at two points on substantially opposite sides of the circumference of the first zone.

The person skilled in the art will understand that the second criterion may be defined such that it must be fulfilled if the first criterion is not fulfilled. The first criterion may thus be a necessary condition for non-fulfilment of the second criteria.

If the first criterion is not fulfilled, the treatment characteristics are changed as described above with respect to the first treatment location. Thus, further HIFU doses are delivered with gradually changing treatment characteristics until the first criterion is fulfilled.

If and when the first criterion is fulfilled, and the second criterion is also fulfilled, the device moves the treatment head to treat a third treatment position. The third treatment position is treated as described here with respect to the second treatment conditions.

If the first criterion is met, but the second criterion is not fulfilled, the device moves the treatment head to treat a third treatment position. The treatment characteristics are changed, however, before delivering a HIFU dose to the third treatment position. For example, the power may be reduced by 25-50 W. Additionally or alternatively, the treatment characteristics may be changed such that no bubble activity, cavitation and/or boiling above a certain threshold occurs and the third treatment location, i.e. the third treatment location is treated as described above with respect to the first treatment location.

It will be understood that the invention is directed to a device adapted to carry out the steps above as well as a method of performing the steps.

In particular, the comparison of the hyperechoic mark with the first and second zone may be done by user, for example by visual inspection of the hyperechoic mark on a screen in comparison with the overlaid first and second zones, or automatically be means of an image analysis software.

Preferably, the device comprises discrete power levels to adjust the HIFU energy delivered by one dose. Particularly preferably, the power is increased by one level at a time until the first criterion is met. Additionally or alternatively, the power is decreased by one or two levels if the second criterion is not met.

Discrete power levels are particularly advantageous for the present invention if HEMs are used to indicate boiling/bubble activity. If boiling is too early and/or strong, it may cause a vein perforation. Contrary to methods where a lesion size is estimated using a HEM, continuous power adaptation is not necessary for the analysis of bubble activity.

Indeed, the aim is to induce boiling, but without having an excessive cavitation activity which could lead to unwanted mechanical damages to the vein or an overly large boiling bubble cloud. The latter may interact with a next pulse and/or cause damages to the perivenous tissues.

Typically, a range of parameters is suitable to achieve the desired advantages. The range may thus be represented by the fulfillment of the first and the second criteria. Thus, the power may be considered to be properly calibrated if the first and the second criteria are fulfilled.

In this respect, the increment between power levels is preferably chosen such that it is smaller than the above-mentioned range. Thus, the increment is small enough to avoid a case where a change of a power level, i.e. an increase by one increment, changes the HEM such that the first criterion is not fulfilled before the change, but the second criterion is not fulfilled after the change. This would schematically correspond to the increment "skipping" the correct range of parameters and going directly from "too weak" to "too strong" in one increment. It should be noted that a change in treatment characteristics in the case where the second criterion is not fulfilled should preferably be large enough so that criterion 2 is fulfilled after a subsequent HIFU dose.

Moreover, continuous power adaptation may require the user to measure the HEM area. Here, the visual assessment is made easier, since the user only has to determine if the HEM is bigger or smaller than certain overlays represented by the first and second zones.

Moreover, HEMs are not easy to segment since they induce artefacts on the B-mode image. Thus, a precise segmentation is very difficult in practice, both by an automatic algorithm and manually. Thus, it is not advantageous to use a continuous power adaptation, because an input of the power adaptation formula would be considerably imprecise despite the seemingly more precise input by the user. Thus, adaptation of power is significantly facilitated for a user with the device described herein.

Preferably, the increment between power levels is constant. Alternatively, it is not constant. For example, it may follow an exponential law. Preferably, the increment is equal to the decrement, alternatively they are different. If they are different, the decrement is preferably bigger in absolute value than the increment.

The first and second zones and/or the first and second criteria may be defined such that they represent a bubble activity suitable for preventing coagulum formation.

In the following, criteria are defined with respect to the "focal spot". It will be understood that the treatment location referred to above may preferably the location of the focal spot. Generally, a focal spot will be understood by the skilled person as a zone where the intensity is larger than −6 dB of the maximum intensity. However, these criteria also apply to other definitions and, in the following, the expression "focal spot" can also be understood as a zone around the point of maximum intensity of the acoustic field, where, cavitation or boiling may occur in the tissue in the conditions of the treatment (power, pulse durations . . . ). These notions can refer to an actual zone (e.g. actual −6 dB focal spot in the tissue), or an estimation based on measurements in a testing environment, in particular in water, computations based on the geometry, simulations, experiments etc. As known by the person skilled in the art, bubble clouds may significantly grow above the focus, leading to what is commonly referred to as a "tadpole-shape lesion", and significant bubble activity can sometimes be detected mainly above the focus. Thus, the focal spot according to the present invention may even not comprise the point of maximum intensity.

In a preferred embodiment, the sonications are delivered on an incompletely collapsed vessel of a size that is smaller, than the focal spot size, in particular that has a smaller cross section than the focal spot and/or has at least one dimension that is smaller than a diameter of the focal spot size. Preferably, the vessel lumen size along the main ultrasound propagation axis is still smaller than twice the −6 dB focal spot size so that significant heating occurs on both sides of the vessel wall (most preferably smaller than the −6 dB focal spot size). Preferably, the vessel lumen size along the main ultrasound propagation axis is greater than 100 µm so there is enough blood inside to allow for bubble activity inside the vein.

An additional advantage arises if the vein is not exactly in the focal spot, but in an area close by. In this case, the formation of bubbles in the blood will enhance the heating in this area. It thus creates an autofocussing effect where the maximal heat absorption occurs not at the spot of maximum intensity, but in an adjacent area. This effect facilitates targeting and is especially useful if the vein is compressed or under spasm and difficult to see with B-mode. This effect is particularly pronounced if the parameters are chosen such that cavitation occurs only in the blood (because it is easier in liquid), and not in surrounding tissues.

The focal spot size, in particular along the main ultrasound propagation axis, can be comprised between 100 µm and 200% of the focal spot size along the main ultrasound propagation axis.

In a preferred embodiment, the focal spot of the HIFU pulses is moved during the sonication. Bubbles hence can be created in a volume bigger than the focal spot size. Thermal coagulation of blood occurring outside the focal spot due to heat diffusion can be prevented.

In a preferred embodiment, one or several markers indicating the acceptable size and/or position of the lumen of the treated vessel, in particular along the main ultrasound propagation axis, are overlaid on a real-time monitoring image. For example, in an embodiment where the size of the lumen along the main ultrasound propagation axis should be smaller than half the size of the focal spot along this axis and the top of the focal spot should be tangent to the deep border of the vein wall, a marker showing the focal spot, or only the top of the focal spot, can be overlaid on the live image to guide vein positioning of the focal spot with respect to the vein. Additionally or alternatively, another marker can be overlaid above the top of the focal spot, at a distance of a half focal spot size along the main ultrasound propagation axis, to guide vein compression.

In another preferred embodiment, the intensity, in particular the intensity of the HIFU pulse, is such that cavitation is only triggered inside the vessel lumen and not in the surrounding soft tissue. Indeed, the cavitation threshold is lower in the blood than in soft tissue.

Preferably the frequency of the ultrasound is between 100 kHz and 5 MHz.

Preferably, the sonications are delivered on a vessel which is not completely collapsed.

For example, collapsing can be performed using an external compression device such as a balloon filled with fluid, by infiltration of fluid into the tissue, or by elevating the patient's leg. Collapsing level is monitored based on the monitoring mean of the treatment (e.g. B-mode imaging).

The intensity of the at least one HIFU pulse may be such that bubble activity is triggered inside the vessel lumen and in the surrounding soft tissue.

Additionally or alternatively, the point of maximum intensity, preferably the focal spot, at the beginning of the pulse is placed below the vein.

In a preferred embodiment, at least part of the vein wall is in the focal spot.

In another preferred embodiment, some tissue above the vein and some tissue under the vein are located in the focal spot.

In yet another preferred embodiment, the whole focal spot is below the vein.

Moreover, it is known from Hynynen (1995) that cavitation can lead to vessel rupture. To avoid the resulting hematomas, it is important to control the cavitation regime. This can be achieved by the steps described in the following. It will be understood by the person skilled in the art that these steps can be used in combination with other methods and/or devices as described herein. However, it is of course also possible to exclusively perform the following steps.

Preferably, this is done by delivering at least a first pulse with characteristics (power, pulse duration . . . ) which are not supposed to induce cavitation or boiling. Then, the characteristics are modified so as to increase the probability of cavitation or boiling until the proper regime is reached. In a preferred embodiment, the pulse characteristics are refined all along the treatment. Indeed, local variations in the tissue properties prevent pulse characteristics from being suitable for the whole treatment. Pulse characteristics refinement can be performed based on a feedback indicating the amplitude of the bubble activity (hyperechoic spots on B-mode imaging, PCD, etc.). For example, a first pulse is delivered at 1 MHz, 5000 W/cm of peak intensity at focus, and no bubble cloud activity is detected. Then, the power is increased so as to obtain 10000 W/cm of peak intensity at focus and a hyperechoic mark is observed on B-mode imaging. As the size of the hyperechoic mark is of a 3 mm by 3 mm in the imaging plane and the targeted vein is within the area of the bubble cloud, the same parameter is used in the next pulses. After a few pulses, the size of the hyperechoic mark becomes above a certain predefined threshold, thus the power is reduced.

In an alternative embodiment, control of the HIFU emission is performed during the pulse based on the analysis of the hyperechoic spot generated on B-mode images by the presence of a bubble cloud. In a preferred embodiment, an US-imaging probe is embedded into the treatment head in order to monitor the zone located around the focal spot. During a HIFU pulse, the HIFU transducer is intermittently switched off for short periods (ranging from 10 microseconds to 500 ms) to acquire B-mode images of the zone around the focus. Despite these short interruptions, this is still considered to be a single HIFU pulse since the temperature in the target does not have the time to significantly decrease. Preferably, at least one B-mode image is acquired during a pulse. At least one (preferably each) image is automatically analysed during the pulse to detect the presence of a bubble cloud. Preferably, a characteristic of the geometry of the hyperechoic spot is automatically computed (for example, its area, or its diameter along a direction). Based on this information, the characteristics of the current pulse are modified. For example, the HIFU emission is switched off if the hyperechoic mark reaches a certain size, or the power is reduced if the bubble cloud appears sooner than predefined values.

In the following, the invention is described in detail by reference to the following figures, showing:

FIG. 1: Schematic drawing of a vein that is treated by HIFU according to the claimed method.

Figure 2:
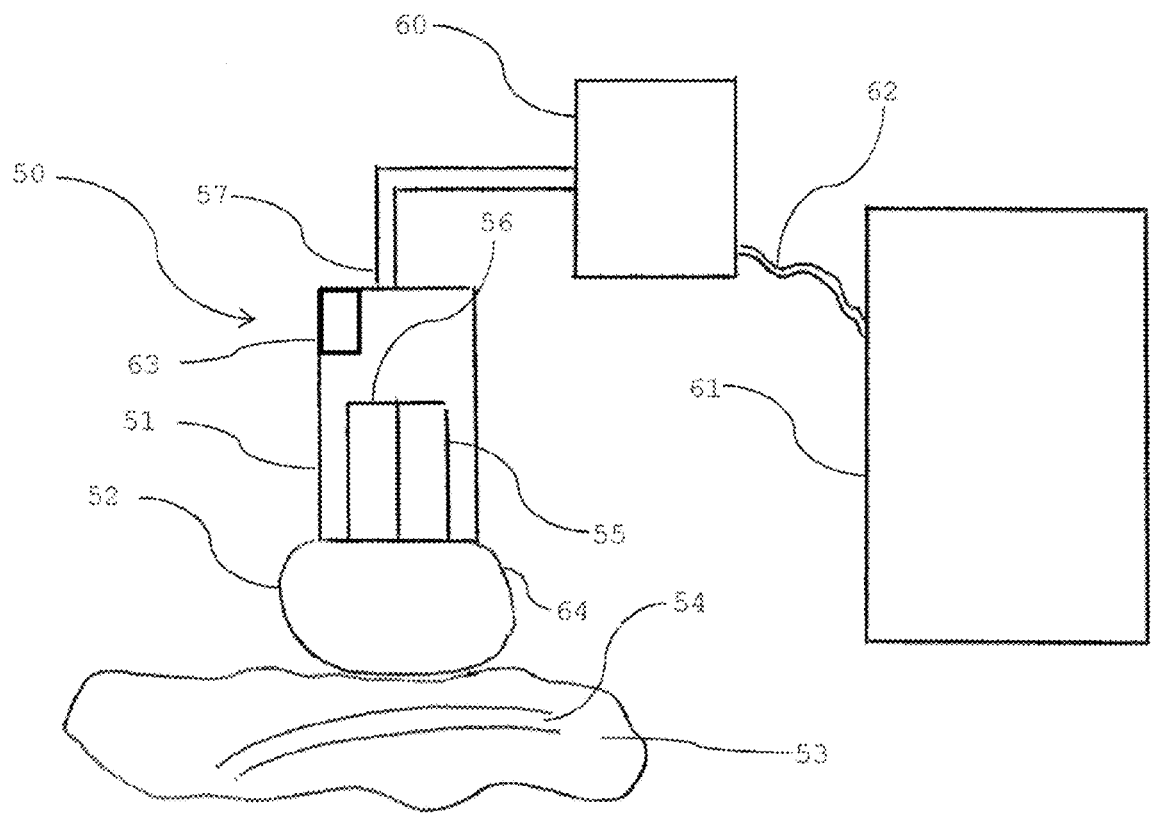

FIG. 2: schematic illustration of an embodiment of a device according to the invention.

Figure 3:
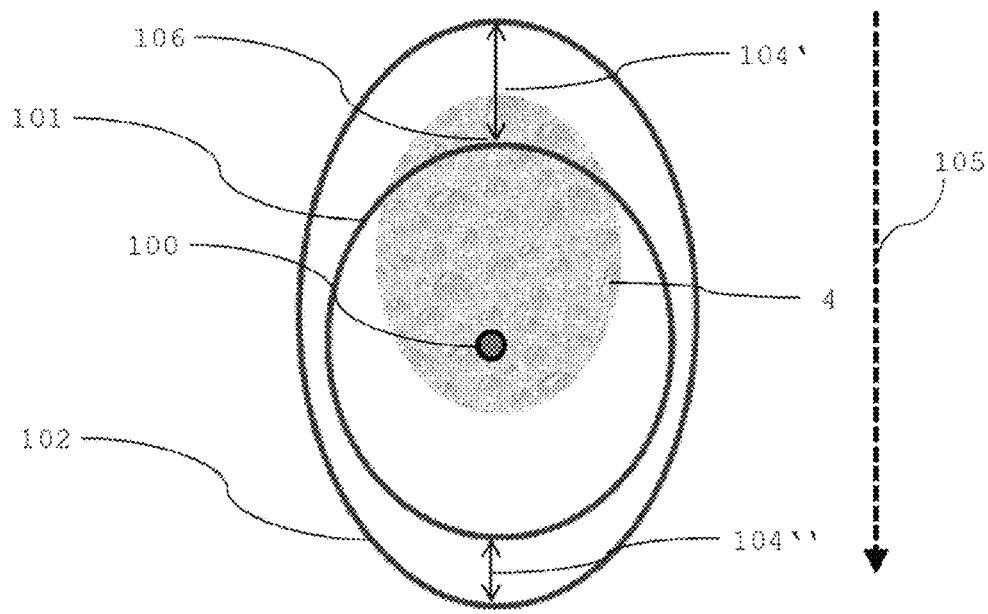

FIG. 3: schematically a bubble cloud with a first and second zone.

FIGS. 4a-4c: schematically a treatment of a first location.

FIGS. 5a-5c: schematically different treatments of a second location.

FIG. 1 schematically shows a vein 6 that is being treated by a HIFU pulse 8. The focal spot 1 is chosen such that it is larger than the vein 6 along the main propagation axis of the ultrasound. In particular, this enables the treatment of both sides of the vein wall 2. Inside the vein lumen 7, the sonication creates bubbles 4 in the blood 3. The creation of a plurality of bubbles leads to micro-streaming 5, which prevents the formation of a blood coagulum.

FIG. 2 shows schematically a device 50 that is adapted to perform the method according to the invention to treat a patient with HIFU. The device 50 comprises a probe head 51 with a treatment transducer 55. The transducer is adapted to deliver ultrasound waves focused onto a target 54 in an object 53. In the present embodiment, the treatment head 51 further comprises a monitoring means 56, for example an ultrasound imaging device. The treatment head further comprises a compression unit 52, here in the form of a membrane 64 that is mounted onto the probe head 51 and forms a cavity for receiving a fluid. The fluid in the cavity is circulated by a pumping system 63. The device further comprises an actuator 60 that is connected to the probe head 51 by an arm 57 and that is adapted to move the treatment head 51. The device also comprises a controller unit 61 that is operatively connected to the transducer 55, the compression unit 52 and the actuator 60, in the present example by means of a cable 62. In particular, the controller unit 61 is adapted to control the intensity of an emitted HIFU pulse.

FIG. 3 schematically shows a bubble cloud 4 caused by a HIFU beam in a tissue. For clarity, no particular tissue is shown here, but it will be understood that the described principle could be applied to any tissue or tissue structure, in particular a tissue structure as shown in FIG. 1 or 2. The HIFU beam was focused on and delivered a HIFU dose to a target location 100. A first zone 101 is defined such as to have a substantially elliptical shape. The target location 100 is positioned within the first zone 101 and substantially coincides with a center of the first zone 101. A second zone 102 is defined such as to fully encompass the first zone 101. The second zone 102 has an elliptical shape, wherein the first and second zones 101,102 are displaced along a treatment axis 105 to reflect a common occurrence where larger HEMs are formed closer to the transducer. As a consequence, a first distance 104' between the circumferences of the first and second zones 101,102 in a direction parallel to the treatment axis is larger than a second distance 104". Here, the bubble cloud 4 has a size smaller to the first zone 101. However, the bubble cloud 4 forms a hyperechoic mark and is shifted in a direction opposite of the treatment axis 105. Therefore, the hyperechoic mark is partially positioned outside the first zone 101. The hyperechoic mark does not extend outside the second zone 102. For example, if a first criterion required a hyperechoic mark with a size equal to or larger than the first zone 101, the first condition would not be met. Alternatively, a first criterion may require that the hyperechoic mark extends over a delimitation 106 of the first zone 101 in a direction opposite of the treatment axis 105 (i.e. towards a treatment head), which would presently be met. Similarly, if a second criterion required that no hyperechoic mark extends beyond the second zone 102, the second criteria would presently be fulfilled.

FIGS. 4a-4c schematically show a treatment of a first treatment location. For clarity, no tissue is shown. A first and second zone 101,102 is defined basically as shown in FIG. 3. However, the first and second zones 101,102 are presently co-centered.

FIG. 4a shows a treated area with the first and second zones 101,102 after delivery of a first HIFU dose. Here, the HIFU dose comprised one pulse with an energy of 100 J. The treatment characteristics were chosen such as to not create a significant bubble activity. Thus, no hyperechoic mark is visible. Thus a next dose with is delivered with an increased energy of 125 J.

FIG. 4b shows the same tissue area as FIG. 4a after delivery of a second HIFU dose. The treatment characteristics, here the energy delivered with the pulse, were increased. As a consequence, a bubble cloud 4 forms that is visible as a hyperechoic mark 107. Here, a first criterion was defined according to which the entire the hyperechoic mark 107 needs to have a surface area at least as large as the first zone 101. Presently, the first condition is thus not fulfilled and the energy is further increased for delivery of a next HIFU dose.

FIG. 4c shows the tissue area of FIGS. 4a and 4b after delivery of a third HIFU dose. The bubble cloud 4 forms a hyperechoic mark 107 that presently fulfills the first criterion because the hyperechoic mark has a larger surface area than the first zone 101. Thus, the treatment at the shown location is terminated and the treatment head is moved to a next location. The treatment characteristics used for the third HIFU dose are saved and used for a first HIFU dose at a next treatment location.

FIGS. 5a-5c show the second treatment location with different possible outcomes of after delivery of a first HIFU dose at the second location.

FIG. 5a shows a situation where the hyperechoic mark 107 formed by the bubbles 4 is smaller than the corresponding hyperechoic mark at the first treatment location (FIG. 4c). Thus, the first criterion is not fulfilled as the hyperechoic mark is smaller than the first zone. This indicates that the delivered HIFU energy was insufficient for the desired treatment effect. Thus, a further HIFU dose may be delivered at the same treatment location with adjusted treatment characteristics, for example a higher power and/or a higher number of pulses, such as to increase the size of the hyperechoic mark.

FIG. 5b shows a situation where the bubble cloud 4 and consequently the hyperechoic mark 107 are larger than the first zone 101, but smaller than the second zone 102. Thus, the first criterion and the second criterion are fulfilled and treatment and this treatment location may be terminated. FIG. 5b corresponds to FIG. 4c for a second treatment location.

FIG. 5c shows a situation where the delivered HIFU energy was larger than intended and expected at a second treatment location. The bubbles 4 and the hyperechoic mark 107 extend over the second zone 102. Thus, the first criterion is fulfilled, but the second one is not. Therefore, the treatment at this location may be terminated and the treatment head is moved to a third location. However, a next HIFU dose at the third location would be delivered with treatment characteristics which lead to less bubble activity. Alternatively, the procedure as shown in FIGS. 4a-4c may be initiated at the third location.

The invention claimed is:

1. A method for treating a patient by thermal ablation of a blood vessel (6) by HIFU, wherein the blood vessel is at least partially collapsed during the thermal ablation, and wherein the treatment is carried out by a sonication with at least one HIFU pulse (8), characterized in that the characteristics of the at least one pulse (8) is chosen such as to create bubbles (4) within the blood (3) inside the vessel (6) and such as to thermally coagulate at least part of the wall (2) of the targeted vessel without coagulating blood, further comprising monitoring a presence of the bubbles, and adapting an intensity of at least one further HIFU pulse based on the presence of the bubbles.

2. The method according to claim 1, wherein the characteristics of the at least one pulse (8) are adapted such as to create bubbles (4) at blood temperatures that do not cause thermal coagulation in the blood (3.

3. The method according to claim 1, wherein an intensity of at the least one HIFU pulse (8) is such that the blood is heated to a blood temperature that would cause thermal coagulation in the absence of bubbles.

4. The method according to claim 1, wherein an intensity of the at least one pulse (8) is such that cavitation (5) is constantly present.

5. The method according to claim 1, wherein the mechanical index of the at least one HIFU pulse (8) is kept above 1.9 during the whole treatment.

6. The method according to claim 1, wherein the creation of bubbles (4) during the at least one HIFU pulse is, intermittently or continuously, triggered by at least one of amplitude modulation and frequency modulation.

7. The method according to claim 1, wherein the monitoring is performed by a monitoring means (56) that is adapted to image the area to be treated.

8. The method according to claim 1, wherein an intensity of the at least one pulse is chosen based on a manual control or automatic feedback loop from the monitoring such as to create bubble activity.

9. The method according to claim 1, wherein the sonication is delivered on an incompletely collapsed vessel (6).

10. The method according to claim 9, wherein the sonication is delivered on a collapsed vessel (6) of size smaller than a focal spot size (1) of the at least one HIFU pulse (8) along an axis of main propagation of the ultrasound.

11. The method according to claim 9, wherein the sonication is delivered on a vessel (6) of a size comprised between 100 μm and 200% of a focal spot size (1) of the at least one HIFU pulse (8) along an axis of main propagation of the ultrasound.

12. The method according to claim 11, wherein the focal spot (1) of the at least one HIFU pulse (8) is moved during the sonication.

13. The method according to claim 1, wherein an acceptable size or position of a lumen of the vessel (7) along the main ultrasound propagation axis is overlaid on a real-time monitoring images.

14. The method according to claim 13, wherein the intensity of the at least one HIFU pulse is such that cavitation (5) is only triggered inside the lumen of the vessel (7) and not in a surrounding soft tissues.

15. The method according to claim 13, wherein the intensity of the at least one HIFU pulse is such that bubble activity (5) is triggered inside the lumen of the vessel (7) and in a surrounding soft tissues.

\* \* \* \* \*